(12) United States Patent
Anderson

(10) Patent No.: US 6,657,443 B2
(45) Date of Patent: Dec. 2, 2003

(54) ABSOLUTE-READING SOIL MOISTURE AND CONDUCTIVITY SENSOR

(75) Inventor: Scott Knudson Anderson, Meridian, ID (US)

(73) Assignee: Technical Development Consultants, Inc., Meridian, ID (US)

( * ) Notice: Subject to any disclaimer, the term of this patent is extended or adjusted under 35 U.S.C. 154(b) by 0 days.

(21) Appl. No.: 09/945,528

(22) Filed: Sep. 4, 2001

(65) Prior Publication Data

US 2003/0042916 A1 Mar. 6, 2003

(51) Int. Cl.[7] ............................................. G01R 27/08
(52) U.S. Cl. ....................... 324/664; 324/640; 324/689
(58) Field of Search ................................ 324/640, 643, 324/663, 664, 689; 73/29.01, 73; 331/135; 239/63, 64, 69

(56) References Cited

U.S. PATENT DOCUMENTS 5,148,985 A * 9/1992 Bancroft ...................... 239/64
5,677,476 A * 10/1997 McCarthy et al. ........... 324/611
5,818,241 A * 10/1998 Kelly .......................... 351/220
6,340,892 B1 * 1/2002 Rynhart et al. .............. 324/640

* cited by examiner

Primary Examiner—Jay Patidar
Assistant Examiner—Donald M Lair
(74) Attorney, Agent, or Firm—Vour Intellectual Property Matters, LLC; Robert Frohwerk

(57) ABSTRACT

A method of sensing moisture based on propagation-delay provides absolute readings of volumetric water content in a moisture-bearing medium without calibrating the sensor or its readings for the conductivity or temperature of the medium. A fast transition is launched on a transmission line that is immersed in the medium to be measured. The amplitude of the resultant waveform is analyzed at precise, programmable time increments by using a high-speed latching comparator. Firmware in a controlling microprocessor facilitates the successive reconstruction of the significant characteristics of the returning waveform. The microprocessor analyzes these characteristics to provide an accurate determination of propagation delay and conductivity, even for severely distorted waveforms. The moisture content of the medium is derived from the propagation delay.

6 Claims, 6 Drawing Sheets

ABSOLUTE-READING SOIL MOISTURE AND CONDUCTIVITY SENSOR

FIELD OF THE INVENTION

This invention relates generally to a method for measuring the moisture content of a bulk material, and specifically to such a method where the bulk material is soil in which turf or crops are cultivated.

BACKGROUND

The disclosed sensing method was designed to provide monitoring of the volumetric soil moisture content and report the same to a controller that activates irrigation valves in a manner so as to automatically irrigate the crops or turf. Many such systems of soil moisture monitors and controllers have been developed in the past with practically no commercial appearance in the irrigation control marketplace. Conductivity sensors, bulk dielectric constant sensors, time domain reflectometer (TDR) type sensors, and various oscillators using the dielectric constant of the water in the soil have been invented and patented with the hope for commercialization, yet acceptance has been marginal. This author has also experimented with and attempted to commercialize several of the above types with marginal results.

The major problem has been the impact of soil conductivity on the readings. Soil conductivity is a function of the ion content of the soil and of its temperature. Salts from irrigation water and/or fertilizer can build up in the soil and cause significant errors in moisture readings. Acidic or alkaline soils also have a detrimental effect on moisture readings taken by capacitive type or propagation type probes. At higher soil temperatures the conductivity increases and the errors become more pronounced.

Because of the uncertainty in the readings caused by this conductivity problem, many of the sensor offerings that have appeared in the marketplace have attempted to get by with 'relative' reading operation. This means that the sensor is installed in the soil (usually with a lot of water) and allowed to come to equilibrium with the surrounding soil for a week or so. A reference reading is then taken from the sensor at a point where the crop is judged to be 'dry' or in need of water. That reference reading becomes the threshold at which the controller is to apply water. It is assumed that whenever the sensor reading gets down to that reference level that the soil moisture is at the same 'dry' condition and is in need of replenishment. Unfortunately the readings from these 'relative' sensors do not remain in synchronism with the true or 'absolute' water content of the soil throughout the season. Ionic material and temperature have a major impact on that relationship and the crops tend to receive insufficient water as the seasonal temperature rise occurs and as salts build up in the soil. The solution to this problem is a sensor that measures the absolute amount of water in the soil under all practical conditions of salt content and temperature.

Based on experience with several types of sensors it was decided to pursue a propagation delay type sensor as the foundation upon which to build the solution. The author had his best experiences with a sensor similar to the one disclosed by Woodhead, et al in U.S. Pat. No. 5,148,125. This type of sensor relies on the fact that the propagation velocity of an electromagnetic wave in water is only 11% of what it is in air. A medium such as soil has a propagation velocity (v) according to:

$$v = c/\{\text{square root } (k)\}$$

wherein c is the velocity of light and k is the relative bulk dielectric constant of the medium. Water has a relative dielectric constant of about 78 at room temperature whereas the other components of soil rarely exceed a relative dielectric constant of 4. The relative bulk dielectric constant of a non-saturated soil-water mixture then ranges from around 4 to around 35 and the propagation velocity of a signal passing through soil ranges from about $0.5c$ to $0.17c$ respectively, being almost entirely dependent upon the water content.

Measuring the propagation time of a signal through soil is complicated by soil conductivity. Herein lies the source of the errors in present propagation-based, capacitance-based and conductivity-based sensors. For propagation-based sensors a transmission line of some sort is used to guide an electromagnetic wave through a specific length of soil. A wave is launched on the transmission line and received on the distant end or reflected back to the transmitter where its propagation time is measured. To simplify the propagation time measurement, the transmitted waveform is usually a pulse or step function with a very fast leading edge. Soil conductivity acts as a shunt loss mechanism to the transmission line. A mathematical analysis of such a model shows that the propagated waveform will have a reduction in amplitude and a dispersion of its leading and trailing edges. A transmitted pulse with 0.1 ns rise time could be received with several nanoseconds rise time and a greatly reduced amplitude. Deriving soil moisture data from such received waveforms has, in the past, been relegated to interpretation by trained personnel. Because of this complexity this method has not been commercialized as a means of automatically gathering soil moisture data.

SUMMARY OF THE INVENTION

This invention provides the means to launch a fast rising edge on a transmission line passing through a specific length of soil. The line folds back to a receiver mounted on the same circuit board as the transmitter. A precise timing and successive approximation amplitude-measuring scheme captures the timing and amplitude of the returning waveform with pico-second and milli-volt resolution, respectively. Front point-by-point waveform measurements, the slope along the returning waveform is examined. The point of the maximum slope is located and the propagation delay amplitude and slope at the maximum slope point are retained. A straight line of the same slope is then projected from the maximum slope point back to the baseline signal reference. The intersection of that line with the baseline reference represents the timing where the first returning energy from the transmitted edge reaches the receiver. This is the inflection point where the received waveform begins to turn upward. The timing of that intersection point is the true signal propagation time. As the slope and waveform amplitude change with soil conductivity that intersection point remains fixed. This intersection point propagation time, along with the dielectric constant of water (corrected for temperature) and the length of the transmission line are then used to calculate the soil moisture. Moisture readings so derived are virtually independent of the effects of ion content and temperature.

DETAILED DESCRIPTION OF THE PREFERRED EMBODIMENTS

Figure 1:
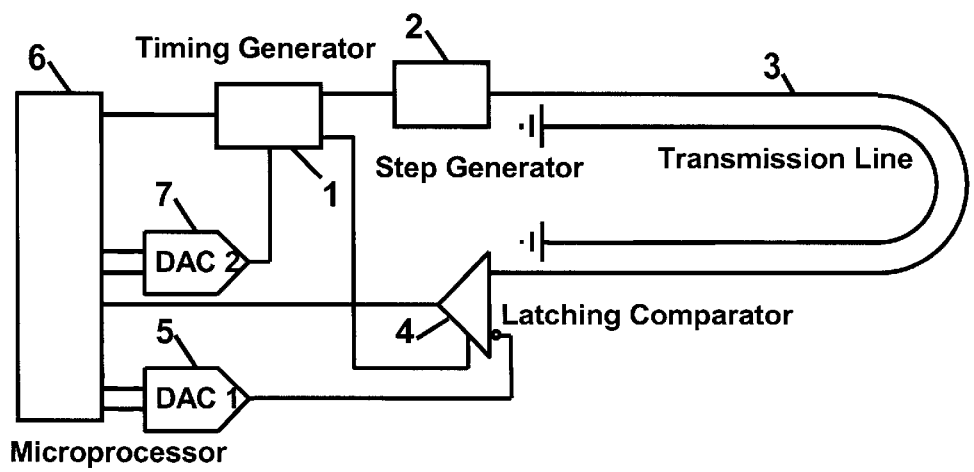
FIG. 1 is a simplified block diagram of the moisture sensor system.

The essential elements of the sensor are diagrammed in FIG. 1. This figure is a simplified block diagram of a precisely-timed waveform generator coupled with a successive approximation amplitude measurement system capable of capturing the detail of very fast waveforms. One of the critical functions in this diagram is that of the timing generator (1). This generator provides two trigger signals that are precisely separated in time by a programmable offset ranging from zero to tens of nanoseconds with a resolution of tens of picoseconds. The offset amount is governed by the setting of a digital to analog converter (7). The offset must be linearly proportional to the DAC input and precisely repeatable from one trigger event to another.

The first trigger activates a step function generator (2). The output of this generator is a very fast rising edge that propagates down the transmission line (3) to the receiving comparator (4). The receiving comparator (4) is a very high-speed analog comparator with latching capability. A component such as the Analog Devices AD96687 may be used. This component captures its binary input state at the instant in time that the second trigger event occurs. The non-inverting input is driven by the incoming waveform from the transmission line (3). The inverting input is driven by the amplitude DAC (5). If the incoming waveform is higher than the DAC setting at the time of the second trigger, then the comparator (4) provides a logical '1' output. If the incoming waveform is lower than the DAC (5) setting, the comparator (4) provides a logical '0' output. The comparator's captured state is then examined by the microprocessor (6). These features make it possible to measure the amplitude of the incoming waveform at a precise time after the waveform was launched. By repeatedly measuring the waveform amplitude at successive time increments, a representation of the entire waveform can be reconstructed, though the moisture-sensing described here does not require that the entire waveform be reconstructed.

Measuring the amplitude at a given time point is accomplished through a successive approximation technique requiring a sequence of waveform launch and receive cycles. The number of cycles required is equal to the number of resolution bits in the amplitude DAC (5). First, the trigger spacing is set in the timing DAC (7). This setting represents the time after the launch of the waveform that the received waveform will be sampled. This setting will remain fixed while the amplitude at this point is found. Next, the amplitude DAC (5) is set to half scale (the most significant bit is set and all others are cleared). Then an output from the microprocessor (6) starts the timing generator (1). The first trigger from the timing generator (1) causes the step generator (2) to launch a step on the transmission line (3). At the precisely programmed interval later the second trigger latches the input to the receiving comparator (4). Next, the microprocessor (6) examines the comparator (4) output. If it is a logical '1' (waveform higher than amplitude DAC), then the microprocessor clears the last amplitude DAC (5) bit setting and sets the next most significant bit. If the comparator (4) output is a logical '0' (waveform lower than amplitude DAC), then the microprocessor leaves the last set bit in its set state and sets the next most significant bit. Then another step function is launched on the transmission line (3). The sequence repeats until all bits in the amplitude DAC (5) have been successively processed from the most significant to the least significant. The resulting amplitude DAC (5) input setting is the digital representation of the waveform amplitude at the precise time that was loaded into the timing DAC (7).

Figure 2:
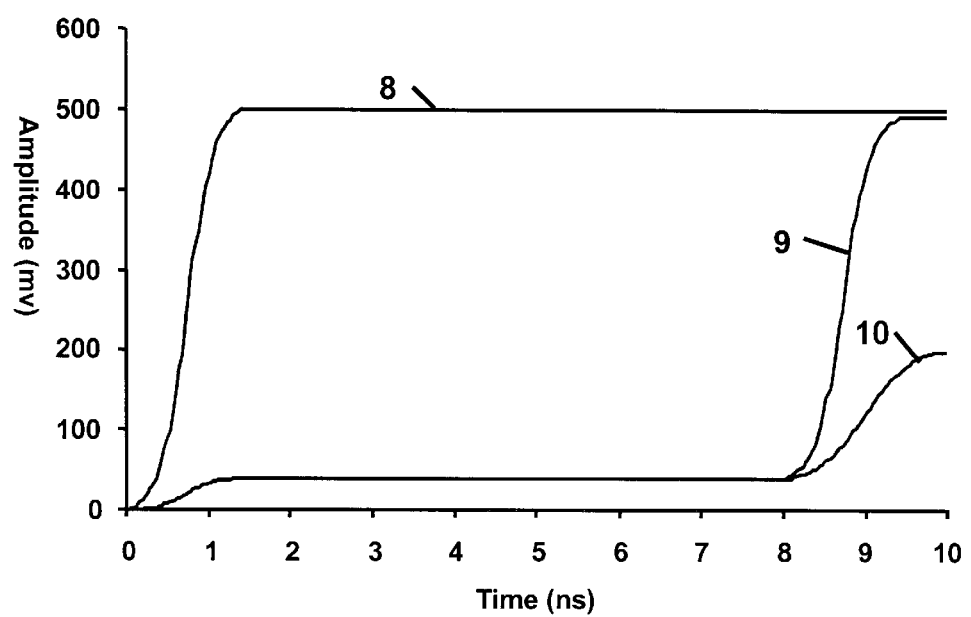
FIG. 2 shows typical waveforms transmitted and received by the moisture sensor.

FIG. 2 represents waveform measurements taken at successive time increments using the aforementioned process. Waveform (8) represents the transmitted step function. Such an image of the transmitted wave can be obtained by connecting the step generator (2) output directly to the receiver comparator (4) input without using the transmission line (3). Waveform (9) represents a waveform that has propagated through moist soil that has low conductivity. Note that waveform (9) is essentially the same as waveform (8) with these differences: The amplitude is slightly lower and the waveform has been translated to the right with a low level signal leading it. This low level signal is the residual feed-through from the step generator (2) directly to the receiver (4). It represents a signal portion that does not travel down the transmission line (3) but couples directly across to the receiver through soil conductivity, electromagnetic coupling and electrostatic coupling. It is of little consequence to the operation of the device and its elimination is not important. The important feature of waveform (9) is the translation relative to waveform (8). Here it is shown to be about 8.0 ns. For a transmission line of 60 cm length this represents a bulk relative dielectric constant of 16.0. That corresponds to a volumetric water content of 20.4% for water at 25 degrees C. The propagation time associated with waveform (9) is easy to measure simply by taking the time differences between it and waveform (8) at corresponding amplitude points.

When soil conductivity becomes significant it becomes much more difficult to measure the propagation time. Waveform (10) represents a signal that has propagated through soil of the same moisture content of waveform (9) but of higher conductivity. The leading edge has been dispersed or broadened and the amplitude has been attenuated. The half-amplitude point, occurring later in time, lies to the right of the half-amplitude point of waveform (9). Finding the right amplitude to measure the true propagation delay is a problem. Attempting to find the inflection point where the wave begins to turn upward is subject to pitfalls due to noise and minor disturbances of the baseline signal. Through much experimentation with various salt, water and soil mixtures at varying temperatures the author has noted that a line constructed through the greatest slope of the rise time of the received waveform intersects the baseline signal level always at the same point for a given bulk dielectric constant. As conductivity increases the amplitude and slope flattens out but a linear projection through the slope back to baseline signal level produces a fixed intercept point. If the similar intercept point from the transmitted wave (8) is known, then the difference between the two becomes the propagation time. The intercept point of the transmitted wave is a constant for a given sensor module and can be programmed into the non-volatile memory of the microprocessor at manufacturing test.

Figure 3:
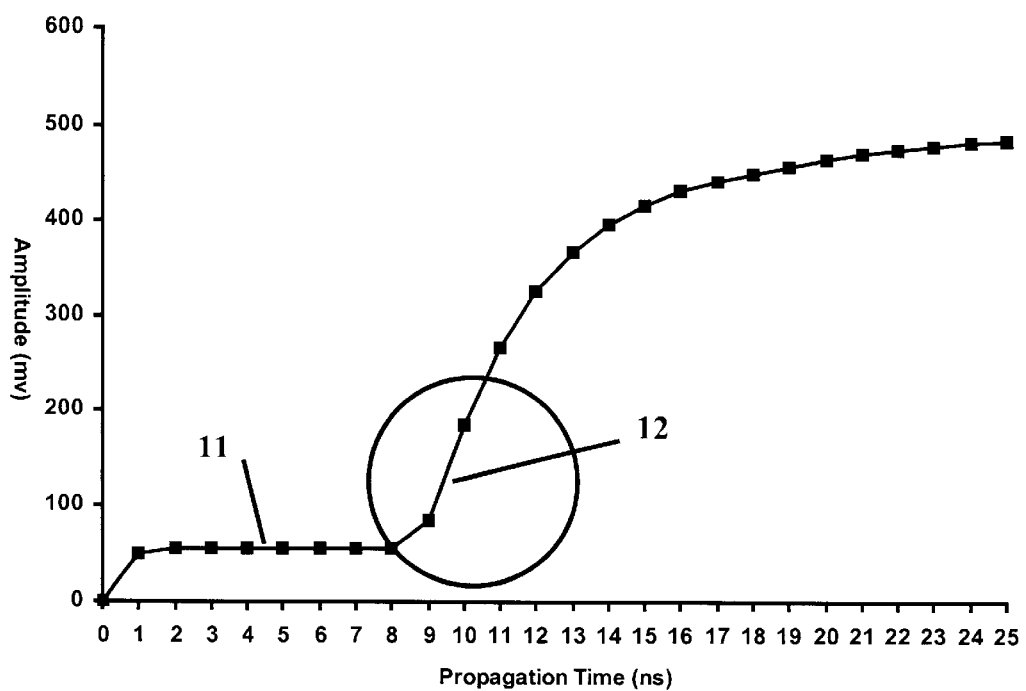
FIG. 3 depicts possible methods used to extract precise propagation delay information from received waveforms.

FIG. 3 is a depiction of the means used to locate and measure the maximum slope of the waveform and to measure its baseline signal level. From these the intercept point can be projected. The waveform in FIG. 3 represents the amplitude of the received waveform as measured at 1.0 ns intervals. In order to capture the approximate location of the rising edge of the returned wave the microprocessor takes amplitude readings at 1.0 ns intervals starting a few nanoseconds above the highest potential propagation time and working backwards at 1.0 ns intervals to the lowest potential propagation time. As each reading is taken it is subtracted from the previous reading. The difference is the amplitude rise per nanosecond for the two points. The timing of the highest difference is retained as the readings progress. In FIG. 3 the highest difference or rate of change is associated with segment 12. The lowest difference to the left of the highest difference is also retained. In FIG. 3 the flat area 11 is the portion of the waveform to the left of the rising edge that has the lowest slope. The amplitude of that area 11 is retained. In this example waveform it is 50 mv.

Figure 4:
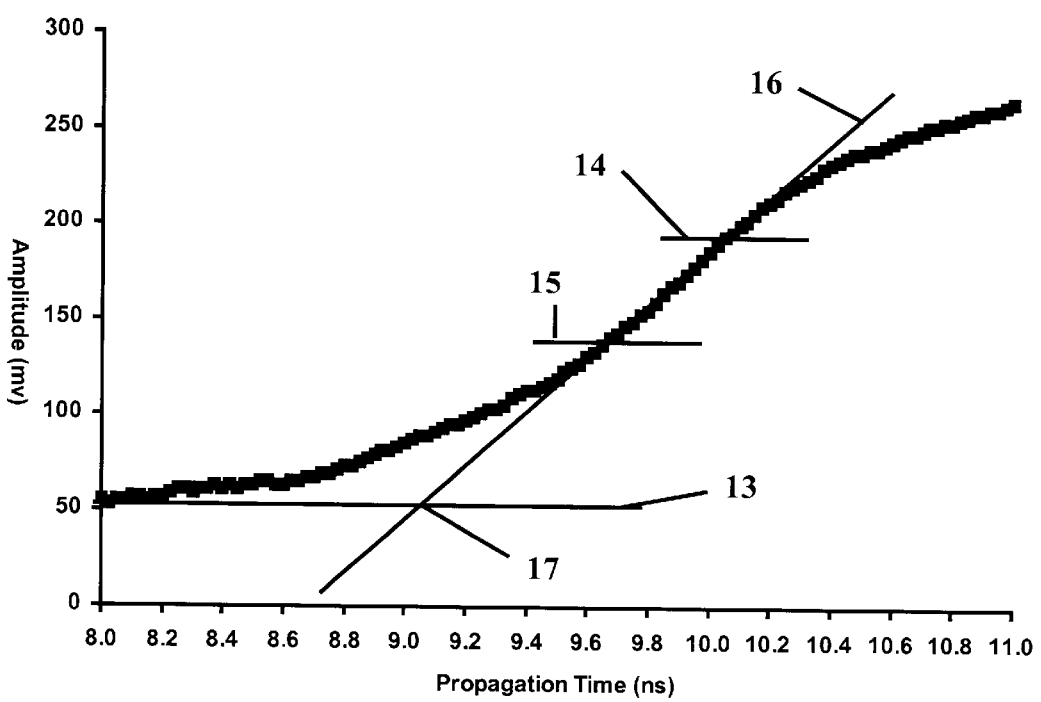
FIG. 4 is an expanded view of a portion of FIG. 3 used to further clarify methods for extracting propagation delay information from the waveform.

After the 1 ns segment with the highest slope has been identified a second pass of measurements is taken around that segment to further refine the measurement and from the refined information to extract precise readings of propagation time and hence soil moisture. Refer to the waveform detail in FIG. 4. In this detail the refined readings are taken at 25 picosecond increments. In order to minimize the effect of noise, the readings are averaged. This is done by passing the successive readings through a 32-word FIFO shift register (created with pointers in firmware). After each new reading, the most recent 16 readings are summed. The average of these 16 readings is represented by the bar 15. The least recent 16 readings are also summed. The average of these readings is represented by the bar 14. The difference between these two sums is proportional to the slope of the waveform at the midpoint between the two groups of readings. As successive readings are taken and these differences are calculated, the greatest difference is retained along with its precise timing and amplitude information. This retained amplitude difference between the averages or centers of the least recent and most recent reading clusters represents the maximum rate of rise of the returned waveform. The midpoint between the two clusters having the greatest difference between their summed readings represents the amplitude where the fastest rise occurs. The time point associated with that midpoint represents the timing of the fastest rise point. The point at which the rising edge of the returned waveform is at its greatest slope is then determined with 25 ps resolution.

The timing at the centers of the two clusters represents the run time associated with the rise. From the run and rise the slope is readily calculated. By projecting the slope backwards (line 16) to its intersection with the waveform baseline (line 13) a crossover point is calculated (point 17). This represents the true propagation delay. As the waveform slope and amplitude vary due to conductivity variations, this intersection remains virtually fixed. Hence a moisture reading is obtained that is independent of soil conductivity. A bonus is created in that the slope of line 16 is a function of soil conductivity. By entering the slope into an empirically derived lookup table the soil conductivity can be retrieved.

Fixed errors remain in the reading due to component tolerances. These are removed through the use of two stored constants that are written into non-volatile memory in the sensor microprocessor during manufacturing. The first constant is an offset. It is derived by connecting the transmitter and receiver directly together and measuring the propagation delay. It represents the propagation delay imbalances in the electronics and is subtracted from the soil readings. The second is a gain constant. It is derived by connecting the transmitter to the receiver through a 20-nanosecond coax cable and measuring the offset-adjusted propagation time. The measured time is divided into 20 ns and the quotient is saved. Subsequent soil readings are then multiplied by this number.

Figure 5:
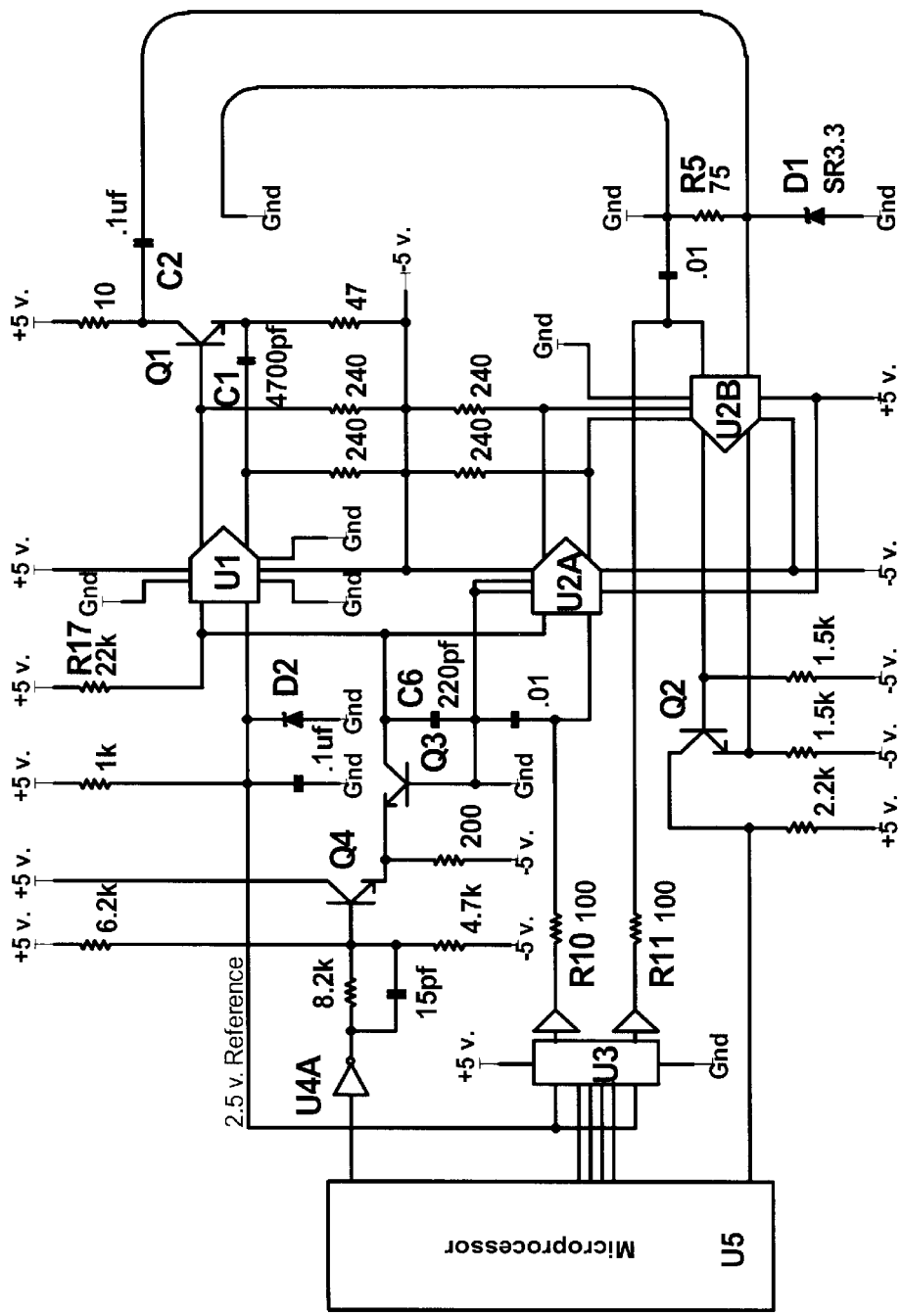
FIG. 5 is a schematic representation of the precision timing and amplitude comparison subsystem in the moisture sensor.

The electronics means used to generate the precisely-spaced dual triggers and to launch and process the waveform is disclosed in FIG. 5. U1, U2A and U2B in FIG. 5 are very high-speed ECL comparators (the AD98685 and AD98687 respectively, both from Analog Devices). C6 is a high quality timing capacitor such as a silver mica capacitor. Q1 is a high current, high gain-bandwidth transistor (Motorola's MMBR571). Q3 and Q4 are likewise high gain-bandwidth transistors (MMBR901, also from Motorola). The microprocessor (U5) used by the author is a PIC16F872 made by Microchip Technology Inc., although many other processors could be used. U3 is a dual 10-bit serial interface digital to analog converter (Analog Devices AD5312). U4A is a high-speed inverting buffer (NC7SZ04, National Semiconductor). D2 is a precision 2.5-volt reference (LM4040-2.5 made by National Semiconductor). D1 is a low capacitance ESD protection device (Semtech's SR3.3).

In the idle state of the system, just before a waveform is launched and measured, the input to U4A is low. U4A biases Q4 such that its emitter voltage is higher than the base voltage of Q3, thus cutting off the collector current of Q3. Capacitor C6 will have been charged to 5 volts through R17 with a time constant of about 5 us. The voltage on C6 is present at the non-inverting input to comparator U1. Since the inverting input is connected to a fixed 2.5-volt reference, the non-inverting output of the comparator will be at the 'high' ECL state whereas the other output will be at an ECL 'low'. This means that transistor Q1 will be on and the voltage on its collector will be about 4.4 volts. Both output channels of the dual DAC (U3) will have been programmed to the appropriate voltages necessary to control the parameters of the measurement. The upper channel of the DAC, connected through R10 to U2A controls the timing between the two precision trigger pulses. The lower channel, connected through R11 to U2B, sets the approximation amplitude for successively narrowing down to the returned signal amplitude.

Figure 6:
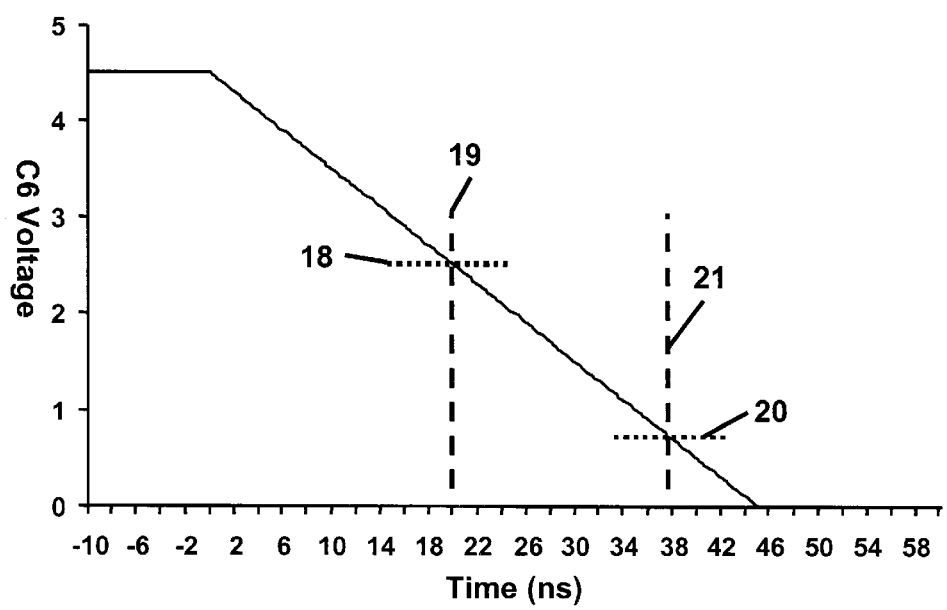
FIG. 6 illustrates the timing ramp and helps to clarify how the spacing between the two precision trigger signals is generated.

The waveform launch and measurement process starts with a high output from the microprocessor to U4A. U4A generates a fast falling edge and quickly turns off Q4 thus turning on Q3, as shown at time=0 in FIG. 6. The collector of Q3 draws a constant 23 ma from C6, thus discharging it at the uniform rate of 0.1 volts per nanosecond as shown in FIG. 6. The downward ramping waveform reaches 2.5 volts after about 20 ns as shown in FIG. 6 (line 18). At this point (line 19) the comparator U1 changes state. The emitter of Q1 is jerked high through C1 while the base is pulled low, thus causing Q1 to quickly shut off. The net effect is a fast rising voltage on the collector of Q1 from 4.4 volts to 5.0 volts in a few hundred picoseconds. This rising edge begins its journey along the transmission line to U2B. It will require a little time to get there depending on the dielectric constant of the medium surrounding the transmission line. It will also become distorted on its journey depending on the conductivity of the medium surrounding the transmission line. While this propagation is going on the ramp on C6 continues to fall at a precise rate. When the ramp voltage equals the output voltage of the upper DAC (U3), as shown by line 20 in FIG. 6, comparator U2A changes state. The time between the state changes on U1 and U2A (difference between lines 19 and 21) is linearly proportional to the capacitance of C6 and the digital input to the upper DAC. It is inversely proportional to the current through Q3. Since C6 and the Q3 collector current are controlled constants, the timing between the events is precisely controlled by the DAC setting.

The outputs of U2A are connected to the high-speed latching inputs of U2B. The change of state of U2A thus latches the input condition of U2B. If the waveform input at the time of the latch signal was higher than the input from the DAC then the collector of Q2 will be a logic high. Otherwise the collector of Q2 will be a logic low. The microprocessor can then use that state to determine the next settings for successively approximating the amplitude of the returning waveform at the propagation time equal to the timing difference between the two triggers.

Other features in the sensor electronics that are not shown in FIG. 5 include a temperature sensor that compensates the readings for temperature variations in the dielectric constant of water and the base-to-emitter voltage of Q3.

In order to reduce power consumption the power to the high-speed comparators and the timing generator circuitry is switched off through MOSFET switches driven by the microprocessor when readings are not being taken. Because of the slow rate at which the moisture content of the soil changes, it is not necessary to continually operate the sensor.

The sensor is interfaced to the controller through a proprietary 2-wire underground power and communications bus. Discussion of the details of that bus is beyond the scope of this disclosure. However, it is important to note that the sensor electronics are electrically isolated from the bus. Power is provided from the bus through an isolated DC-DC converter and communications between the microprocessor and bus are conveyed through transformer and/or opto-isolator coupling. The need for isolation arises from the potential for damage to the sensor electronics during electrical storms. When lightening strikes the ground potential in the vicinity of the strike rises relative to the earth potential some distance away. The charge deposited by the lightening creates this potential difference that remains for a short period until the charge is dissipated into the surrounding area. If high-conductivity means are present in the strike vicinity, such as underground copper wires, they become an ideal discharge path. The charge can enter through the exposed transmission line, work its way through the sensor electronics onto the copper wire bus, then enter a distant sensor and work through its electronics out to its transmission line where the charge is dissipated into the soil. The result is two damaged sensors. Isolation breaks up that conduction path and prevents the damage up to a few thousand volts of potential rise. Protection device D1 prevents ESD breakdown of U2B under such conditions and in normal handling.

Although the present invention has been described here with reference to particular embodiments incorporating specific circuitry, it should be apparent to those of ordinary skill in the art that there are a host of other designs that can be implemented in keeping with the intent of the disclosed invention. The selection, design and arrangement of the various components described here may be modified without departing from the spirit and scope of the invention as represented in the attached claims. For example, although a microprocessor-based system has been shown, other configurations involving various combinations of hardware and software could also be used to accomplish the necessary logical decisions described here.

What is claimed is:

1. A method for digitizing portions of a waveform sent through a moisture-bearing medium comprising the steps of:
   a) providing a transmission line that passes through the medium to a latching comparator;
   b) launching a fast transitioning waveform onto said transmission line; and
   c) measuring the amplitude of a resultant waveform at a programmed point in time at said latching comparator by using a technique involving generation of timing strobes in conjunction with a measurement of amplitude by successive approximation, said technique comprising the steps of:
      c1) providing a programmable voltage reference to which said resultant waveform is compared by said latching comparator;
      c2) providing a programmable time offset for generation of a precisely-timed sampling strobe after the launching of said fast-transitioning waveform in order to sample said resultant waveform amplitude at said latching comparator;
      c3) launching a multiplicity of said fast-transitioning waveform onto said transmission line and adjusting said programmable voltage reference in the manner of said successive approximation until an amplitude representative of a composite of resultant waveform at the given point in time has been acquired; and
      c4) changing the programmable time offset to a next desired point in time and repeating steps c1 through c3 in order to acquire another amplitude representative of a multiplicity of resultant waveform at said next desired point in time until said portions of a waveform have been digitized.

2. The method in claim 1, wherein the propagation time of said fast-transitioning waveform through said medium is calculated from said portions of a waveform, comprising the steps of:
   (a) determining a baseline reference level from a first set of points within said portions of a waveform;
   (b) determining a characteristic slope of transition of said resultant waveform from a second set of points within said portions of a waveform;
   (c) locating a point of maximum slope of transition of said resultant waveform;
   (d) projecting a straight line having said characteristic slope of transition through said point of maximum slope to said baseline reference level; and
   (e) finding an intercept point of said straight line at said baseline reference level, wherein the time associated with the intercept point represents said propagation time of said fast-transitioning waveform through said medium.

3. The method of claim 2, wherein said propagation time is used to calculate a value for the bulk dielectric constant of said medium in contact with said transmission line.

4. The method of claim 2, wherein said characteristic slope of transition of said resultant waveform is used to determine a value for the conductivity of said medium in contact with said transmission line.

5. The method of claim 1, wherein the sensor electronics are electrically isolated from the power source and communications means.

6. The method of claim 1, wherein said medium is soil.

* * * * *

UNITED STATES PATENT AND TRADEMARK OFFICE
CERTIFICATE OF CORRECTION

PATENT NO. : 6,657,443 B2  Page 1 of 1
DATED : December 2, 2003
INVENTOR(S) : Scott Knudson Anderson It is certified that error appears in the above-identified patent and that said Letters Patent is hereby corrected as shown below:

Title page,
Item [54], Title, "SENSOR" should be -- SENSING METHOD --.
Item [74], *Attorney, Agent or Firm*, "Vour" should be -- Your --.
Item [57], ABSTRACT,
Line 2, "absolute readings" should be -- absolute measurements --.
Line 11, "returning" should be -- resultant --.

Column 2,
Line 41, "Front" should be -- From --.
Line 43, insert -- , -- (comma) after "delay".
Line 53, insert -- , -- (comma) after "conductivity".

Column 3,
Line 48, insert -- method -- after "moisture-sensing".

Column 5,
Line 25, "effect" should be -- effects --.

Column 6,
Line 62, insert -- , -- (comma) after "going on".

Column 7,
Line 20, insert -- , -- (comma) after "consumption".
Line 36, insert -- , -- after "strikes --

Column 8,
Line 4, "the" should be -- said --.

Signed and Sealed this

First Day of June, 2004

JON W. DUDAS
*Acting Director of the United States Patent and Trademark Office*